United States Patent
Yamamoto et al.

[11] Patent Number: 5,738,802
[45] Date of Patent: Apr. 14, 1998

[54] FLUORINE-BASED MAGNETIC FLUID

[75] Inventors: Yasushi Yamamoto, Tsukuba; Yoshiyuki Takeishi, Tsuchiura; Yutaka Kouda; Tomoko Minagawa, both of Tsukuba; Takao Kanno, Tokyo, all of Japan

[73] Assignee: NOK Corporation, Tokyo, Japan

[21] Appl. No.: 800,784

[22] Filed: Feb. 14, 1997

[30] Foreign Application Priority Data

Feb. 22, 1996 [JP] Japan .................. 8-060058
Apr. 24, 1996 [JP] Japan .................. 8-127865
Sep. 26, 1996 [JP] Japan .................. 8-273970

[51] Int. Cl.$^6$ ...................................... H01F 1/44
[52] U.S. Cl. .................. 252/62.56; 252/62.52; 252/62.54
[58] Field of Search ............. 252/62.52, 62.54, 252/62.56

[56] References Cited

U.S. PATENT DOCUMENTS 3,784,471  1/1974  Kaiser ................ 252/62.56

*Primary Examiner*—Alan Diamond
*Attorney, Agent, or Firm*—Barnes & Thornburg

[57] ABSTRACT

A fluorine-based magnetic fluid, which comprises (A) fine magnetic particles dispersed in (D) a perfluoropolyether base oil represented by the following general formula:

$$F(CF(CF_3)CF_2O)_m Rf$$

where Rf is a perfluoroalkyl group, by means of (B) a perfluoroether carboxylic acid or salt thereof represented by the following general formula:

$$F(CF(CF_3)CF_2O)_n CF(CF_3)COOM$$

where M is a hydrogen atom, an alkali metal or an ammonium group, and (C) a perfluoroether compound represented by the following general formula:

$$F(CF(CF_3)CF_2O)_p CF(CF_3)X(RO)_q CH_2 COOM',$$

$$F(CF(CF_3)CF_2O)_p CF(CF_3)(Y)_r R'OSO_3M' \text{ or}$$

$$(F(CF(CF_3)CF_2O)_p CF(CF_3)(Y)_r(R)_w O)_s PO(OM')_t.$$

Fluorine-based magnetic fluid has a high affinity of the fine magnetic particles toward the perfluoropolyether base oil and is effectively used as a sealing material for vacuum apparatus.

12 Claims, No Drawings

FLUORINE-BASED MAGNETIC FLUID

BACKGROUND OF THE INVENTION

1. Field of the Invention

The present invention relates to a fluorine-based magnetic fluid, and more particularly to a fluorine-based magnetic fluid comprising fine magnetic particles as dispersed in a perfluoropolyether base oil.

2. Description of Related Art

U.S. Pat. No. 3,784,471 discloses a fluorine-based magnetic fluid comprising surfactant-adsorbed, fine ferrite particles as dispersed in a perfluoropolyether base oil, where perfluoropolyether carboxylic acid represented by the following general formula:

$$F[CF(CF_3)CF_2O]mCF(CF_3)COOH$$

where m is an integer of 3 to 50, or its ammonium salt, etc. is used as the surfactant adsorbed on fine ferrite particles.

However, mere dispersion of such perfluoropolyether carboxylic acid surfactant-adsorbed, fine ferrite particles in the perfluoropolyether base oil has a poor dispersibility and a considerably large amount of poorly dispersed fine particles in the base oil, resulting in a considerable decrease not only in the magnetic fluid yield, but also in saturation magnetization of the resulting magnetic fluids, that is, poor practical applicability, as shown in Comparative Examples which follow. Furthermore, the above-mentioned U.S. Patent discloses that the dispersibility is poor when the m value of the perfluoropolyether carboxylic acid or its salts is smaller.

SUMMARY OF THE INVENTION

An object of the present invention is to provide a fluorine-based magnetic fluid having a higher affinity of fine magnetic particles toward a perfluoropolyether base oil and an effective application as a sealing material for vacuum apparatus, etc.

According to the present invention, there is provided a fluorine-based magnetic fluid, which comprises; (A) fine magnetic particles as dispersed in (D) a perfluoropolyether base oil by means of (B) a perfluoroether carboxylic acid or salt thereof represented by the following general formula:

$$F[CF(CF_3)CF_2O]nCF(CF_3)COOM$$

where M is a hydrogen atom, an alkali metal or an ammonium group; and n is an integer of 1 to 100, and (C) a perfluoroether compound, represented by the following general formula:

① $F[CF(CF_3)CF_2O]pCF(CF_3)X(RO)_qCH_2COOM'$,

② $F[CF(CF_3)CF_2O]pCF(CF_3)(Y)rR'OSO_3M'$ or

③ $\{F[CF(CF_3)CF_2O]pCF(CF_3)(Y)v(R)wO\}tPO(OM')u$ where R is a lower alkylene group; M' is a hydrogen atom, an alkali metal, an alkaline earth metal or an ammonium group; X is COO group or CH₂O group; Y is COO group or CONH group; p and q are an integer of 1 to 100, respectively; r is 0 or 1; t is 1 or 2; u is 3-t; v and w are 0 or 1, respectively.

DETAILED DESCRIPTION OF THE INVENTION

Fine magnetic particles for use in the present invention are generally fine ferrite particles, prepared by any appropriate methods, preferably by a coprecipitation method having advantages of controlling their purity and particle size, particularly their productivity. The preferable fine ferrite particles prepared by the coprecipitation method include, for example, fine particles of magnetite ($Fe_3O_4$) nickel ferrite ($NiO \cdot Fe_2O_3$), manganese ferrite ($MnO \cdot Fe_2O_3$), cobalt ferrite ($CoO \cdot Fe_2O_3$), nickel-zinc ferrite ($Ni \cdot ZnO \cdot Fe_2O_3$), manganese-zinc ferrite ($Mn \cdot ZnO \cdot Fe_2O_3$), cobalt-zinc ferrite ($Co \cdot ZnO \cdot Fe_2O_3$), etc.

Besides, fine particles of such a metal as iron, manganese, nickel, cobalt, etc. or their borides, nitrides, carbides, etc. or furthermore fine particles of alloys of these metals with at least one of such other metals as magnesium, aluminum, zinc, copper, niobium, molybdenum, gallium, indium, zirconium, cadmium, tin, etc. or their borides, nitrides, carbides, etc, can be also used as fine magnetic particles.

Generally, fine magnetic particles have a high hydrophilic property and accordingly undergo coagulation as such in a base oil, resulting in a failure to form a magnetic fluid. Thus, it is necessary to make the surfaces of fine magnetic particles have a higher affinity toward a base oil, thereby preventing their coagulation. Compounds for use to enhance the affinity toward a base oil and prevent the coagulation must have preferably a fluorophilic group and a polar group having a strong adsorbability to ferrites in one molecule at the same time. In view of the necessity for a long chain having some elasticity to prevent coagulation of fine particles and a good solubility or dispersibility in a solvent, compounds having a perfluoroether group as a fluorophilic group are selected.

In the present invention, a perfluoroether carboxylic acid or salt thereof having the above-mentioned general formula has been ultimately selected from these viewpoints. The salt of perfluoroether carboxylic acid can be obtained by hydrolysis of an alkyl ester of carboxylic acid derived from a hexafluoro-propene oxide oligomer having a repetition unit n of 1 to 100, preferably 4 to 50, by an aqueous solution of sodium hydroxide, potassium hydroxide, ammonia or the like. Preferable upper limit to 50 in the repetition unit n is so selected that, when n is above 50, the resulting magnetic fluid has poor characteristics (viscosity, etc.). Free carboxylic acid can be obtained by acidifying the salt of perfluoroether carboxylic acid with a mineral acid such as hydrochloric acid, sulfuric acid, etc.

As described above, single use of perfluoroether carboxylic acid (salt) suffers poor dispersibility, and thus a perfluoroether compound represented by the general formula ①, ② or ③ is used together with the perfluoroether carboxylic acid (salt).

Perfluoroether (poly)alkylene ether carboxylic acid (salt) represented by the general formula ① can be readily obtained according to the following two-steps synthesis method:

I. Synthesis of perfluoroether (poly)alkylene ether:

(1) In case that X is a COO group:

Perfluoroether (poly)alkylene ether having the following formula:

$$F[CF(CF_3)CF_2O]pCF(CF_3)COO(RO)qH$$

where p for the repetition unit is an integer of 1 or more, preferably about 4 to about 50, and q for the repetition unit is an integer of 1 to 100, preferably 1 to 30, can be synthesized by esterification reaction of an acid fluoride having the following general formula, derived from hexafluoropropene oxide oligomer:

$$F[CF(CF_3)CF_2O]pCF(CF_3)COF$$

where p has the same meaning as defined above, with (poly)alkyleneglycol having the following general formula:

$$HO(RO)_qH$$

where q has the same meaning as defined above, preferably polyethyleneglycol or polypropyleneglycol, through dehydrofluorination reaction, or by transesterification of an alkyl ester of carboxylic acid derived from hexafluoropropene oxide oligomer with the above-mentioned (poly)alkyleneglycol.

(2) In case that X is a $CH_2O$ group:
Perfluoroether (poly)alkylene ether having the following formula:

$$F[CF(CF_3)CF_2O]_pCF(CF_3)CH_2O(RO)_qH$$

where p and q have the same meanings as defined above, can be synthesized by etherification reaction of an alcohol having the following general formula, which is obtained by reaction of the above-mentioned carboxylic acid derived from hexafluoropropene oxide oligomer by a reducing agent such as $LiAlH_4$, $NaBH_4$, etc.:

$$F[CF(CF_3)CF_2O]_pCF(CF_3)CH_2OH$$

where p has the same meaning as defined above, with the above-mentioned (poly)alkyleneglycol, using a dehydration catalyst such as sulfuric acid, etc.

II. Synthesis of perfluoroether (poly)alkylene ether carboxylic acid (salt):
Sodium carboxylates having the following general formulae:

$$F[CF(CF_3)CF_2O]_pCF(CF_3)COO(RO)_qCH_2COONa$$

$$F[CF(CF_3)CF_2O]_pCF(CF_3)CH_2O(RO)_qCH_2COONa$$

where p and q have the same meanings as defined above, can be obtained by reaction of the perfluoroether (poly)alkylene ether obtained in the foregoing process I with sodium monochloro-acetate $ClCH_2COONa$ and an alkali hydroxide. These sodium salts can be converted to the corresponding free carboxylic acid by acidification with a mineral acid such as hydrochloric acid, sulfuric acid, etc. and the free carboxylic acids can be subjected to exchange with cation species by neutralization with other alkali metal, alkaline earth metal or ammonia.

Perfluoroether sulfuric acid ester (salt) represented by the above-mentioned general formula ② can be prepared by sulfuric acid esterification of condensation product of a carboxylic acid derived from hexafluoropropene oxide oligomer with p for the repetition unit being an integer of 1 or more or its derivatives with a diol or amino alcohol, or by sulfuric acid esterification of an alcohol obtained by reduction of a carboxylic acid derived from hexafluoropropene oxide oligomer or its derivatives.

Perfluoroether phosphoric acid ester (salt) represented by the above-mentioned general formula ③ can be readily obtained by a known method for synthesizing phosphoric acid ester, using the hexafluoropropene oxide oligomer, where not only single mono- or di-ester, but also a readily formable mixture thereof can be used as such.

The magnetic fluid can be prepared by dispersing fine magnetic particles into a perfluoropolyether base oil in the presence of (B) the perfluoroether carboxylic acid (salt) and (C) the perfluoroether compound ①, ② or ③. About 10 to about 100 parts by weight, preferably about 20 to about 50 parts by weight, of the perfluoroether carboxylic acid (salt) is used per 100 parts by weight of the fine magnetic particles, and about 1 to about 150 parts by weight, preferably about 10 to about 80 parts by weight, of the perfluoroether compound of the general formula ① or ③, or about 0.1 to about 50 parts by weight, preferably about 1 to about 20 parts by weight, of the perfluoroether compound of the general formula ②, is used per 100 parts by weight of the perfluoropolyether base oil. These Components (B) and (C) can be added at the same time or in any desired sequence.

Perfluoropolyether base oil represented by the following general formula:

$$F[CF(CF_3)CF_2O]_mRf$$

where Rf is a perfluoroalkyl group, preferably a perfluoroalkyl group having 1 to 3 carbon atoms; and m is an integer of 1 or more, preferably 10 to 50 (on average), can be used in the present invention. Practically, commercially available perfluoropolyether oil such as BARRIERTA series, trademark of a product made by NOK Kluber K. K., Japan, etc. can be used.

Dispersion treatment can be carried out by the ordinary method using a homogenizer, a ball mill, ultrasonic wave application, etc. A dispersion can be more readily prepared when a fluorinated organic solvent such as Fluorinert FC-72 (trademark of a product made by Sumitomo-3M K. K., Japan) is used at the same time. In that case the organic solvent is distilled off after the preparation of the dispersion. Then, the dispersion is subjected to centrifuge to remove poorly dispersed fine particles therefrom, whereby a magnetic fluid can be obtained.

By using a salt of perfluoroether carboxylic acid and amide compounds of perfluoroether carboxylic acid together in preparation of a fluorine-based magnetic fluid comprising fine magnetic particles as dispersed in a perfluoropolyether base oil, a magnetic fluid of good dispersion can be obtained. The fluorine-based magnetic fluid thus obtained is effective for minimizing changes in vacuum degree and torque, when used as a sealing material for a vacuum apparatus with a shaft, etc.

PREFERRED EMBODIMENTS OF THE INVENTION

The present invention will be described in detail below, referring to Examples and Comparative Examples.

EXAMPLE 1

A mixture consisting of the following Components (A) to (D) was subjected to a dispersion treatment under application of ultrasonic waves for 24 hours, whereby 39.5 g of fluorine-based magnetic fluid was obtained:

(A) Coprecipitation process fine magnetite particles: 4 g (particle size: 90 Å)

(B) $F[CF(CF_3)CF_2O]_nCF(CF_3)COONa$ (n: 8 on average): 1 g (C) $F[CF(CF_3)CF_2O]_pCF(CF_3)COO(CH_2\ CH_2O)_qCH_2COONa$: 5 g (p: 15 on average, q: 6.8 on average)

(D) Perfluoropolyether base oil: 30 g (BARRIERTA J100V)

The Component (B) was obtained by dropwise adding 50 g (0.03 moles) of methyl ester of hexafluoropropene oxide oligomer carboxylic acid (n: 8 on average) to an aqueous solution containing 5 g (0.13 moles) of sodium hydroxide in 100 ml of water at 80° C. at a trickling rate of 1 ml/min. with stirring, continuing the stirring for 5 hours while keeping that temperature, then leaving the reaction solution to stand for cooling, adding about 50 g of sodium chloride thereto, and recovering precipitated white solid by filtration, followed by drying, dissolution into methanol, filtration and distilling off of methanol under reduced pressure[amount of the product: 48.0 g (yield: 96.4%)].

The Component (C) was obtained by dropwise adding 26.7 g of methyl ester of hexafluoropropene oxide oligomer carboxylic acid (n: 15 on average; terminal group: —COOCH$_3$) to a solution containing 6.4 g of polyethyleneglycol HO(CH$_2$CH$_2$O)qH (q: 6.8 on average) and 0.1 g of sodium methoxide in 100 g of diglyme, and heated at 80° C. with stirring for 5 hours, while removing the generated methanol therefrom. After distilling off of the solvent, simultaneous extraction with 200 ml of a cold aqueous NaCl saturated solution admixed with 10 ml of 1N hydrochloric acid and with 200 ml of fluorine-based solvent (Fluorinert FC72) was carried out. Such extractions was repeated twice. Then, the solvent was distilled off from the extract (fluorine-based solvent layer), whereby 27.2 g of an intermediate product [terminal group: —COO(CH$_2$CH$_2$O)$_5$H] was obtained (yield: 93%).

30 g of methanol containing 0.5 g of sodium hydroxide as dissolved therein was dropwise added to a solution containing the intermediate product in 100 ml of diglyme, and 30 g of methanol containing 1.3 g of sodium monochloroacetate was slowly dropwise added thereto while cooling the mixture to 0° C., and the mixture was stirred for 30 minutes. Then, the temperature was elevated to 40° C. and stirring was continued for further 2 hours. Then, the solvent was distilled off therefrom, and the residues were subjected to simultaneous extraction with 200 ml of an aqueous NaCl saturated solution and with 200 ml of a fluorine-based solvent (Fluorinert FC72). The extract (fluorine-based solvent layer) was thoroughly dried over anhydrous sodium sulfate, followed by distilling off of the solvent, whereby 27.3 g of the above-mentioned Component (C) was obtained (yield throughout all the steps: 91%).

The fluorine-based magnetic fluid thus obtained was filled into a space formed between a shaft having 15 mm in diameter and a seal assembly of pole piece-piece as inserted a piece as inserted along the shaft to make a vacuum seal, and then the vacuum seal was placed in a vacuum seal-evaluating apparatus and put into a continuous operation under such conditions of 0.01 Torr and 1,000 rpm for 500 hours to determine the vacuum degree and torque. It was found that there was no change in the vacuum degree with the percent torque change being less than 5%.

EXAMPLE 2

In Example 1, the same molar amount of polyethyleneglycol (q: 4.5 on average) was used Component (C) in place of the poly-ethyleneglycol (q: 6.8 on average), and similar results were obtained.

EXAMPLE 3

In Example 1, the same amount of the same compound with different n (n: 15 on average) was used as Component (B), and similar results were obtained.

EXAMPLE 4

In Example 1, 39.8 g of a fluorine-based magnetic fluid was prepared by using the same amount of the following Component (C):

F[CF(CF$_3$)CF$_2$O]$_p$CF(CF$_3$)CH$_2$O(CH$_2$CH$_2$O)$_q$CH$_2$COONa where p is 15 on average and q is 4.5 on average.

The Component (C) was prepared in the following manner:

A solution containing 26.5 g of free carboxylic acid (terminal group: —COOH) obtained by hydrolysis of methyl ester of hexafluoropropene oxide oligomer carboxylic acid (n: 15 on average) in 100 g of diglyme was cooled to 0° C., and 30 g of diglyme containing 1.2 g of LiAlH$_4$ as dissolved therein was slowly dropwise added thereto with stirring for 3 hours. Then, the reaction mixture was heated to 40° C. and stirring was continued for further 3 hours. Then, the reaction mixture was cooled again to 0° C., and 10 g of water was carefully dropwise added thereto. The solvent was distilled off therefrom, and 100 g of a fluorine-based solvent (Fluorinert FC72) was added to the residues to dissolve them. Insoluble matters were filtered off, whereby a solution of hexafluoropropene oxide oligomer alcohol derivative (terminal group: —CH$_2$OH) was obtained.

To the solution of the alcohol derivative were added 11 g of polyethyleneglycol HO(CH$_2$CH$_2$O)qH (q: 4.5 on average), 10 g of concentrated sulfuric acid and 150 g of diglyme. The mixture was heated to 120° C. with vigorous stirring to distill off the fluorine-based solvent (Fluorinert FC72). Reaction was conducted for 5 hours, while maintaining the reaction mixture at 120° C., followed by cooling to room temperature and neutralization with an aqueous sodium hydrogen carbonate saturated solution. After most of the solvent was distilled off, simultaneous extraction with 200 ml of an aqueous NaCl saturated solution and with 200 ml of a fluorine-based solvent (Fluorinert FC72) was carried out. The solvent was distilled off from the extract (fluorine-based solvent layer), whereby 21.1 g of an intermediate product [terminal group: —CH$_2$O(CH$_2$CH$_2$O)$_5$H] was obtained (yield: 74%).

A solution containing 0.4 g of sodium hydroxide in 30 g of methanol was dropwise added to a solution containing the thus obtained intermediate product in 100 g of diglyme, and then the mixture was cooled to 0° C. Then, a solution containing 1.0 g of sodium monochloroacetate in 30 g of methanol was slowly dropwise added thereto with stirring for 30 minutes, and the reaction mixture wss heated to 40° C. Stirring was continued for further 2 hours and then the solvent was distilled off. Simultaneous extraction of the residues with 200 ml of an aqueous NaCl saturated solution and with 200 ml of a fluorine-based solvent (Fluorinert FC72) was carried out. The extract (fluorine-based solvent layer) was thoroughly dried over anhydrous sodium sulfate, and then the solvent was distilled off therefrom, whereby 21.3 g of the above-mentioned Component (C) was obtained (yield throughout all the steps: 73%).

The magnetic fluid thus obtained was subjected to measurement of vacuum degree and torque in the same manner as in Example 1. It was found that there was no change in the vacuum degree with the percent torque change being less than 5%

Comparative Example 1

In Example 1, the Component (C) was not used at all. Dispersibility of fine magnetic particles was so poor that no magnetic fluid was obtained.

Comparative Example 2

In Example 3, the Component (C) was not used at all. A magnetic fluid was obtained, but the vacuum degree was lowered to 10 Torr with the percent torque change being more than 10%.

EXAMPLE 5

A mixture consisting of the following Components (A) to (D) was subjected to a dispersion treatment under application of ultrasonic waves for 24 hours, whereby 39.5 g of fluorine-based magnetic fluid was obtained:

(A) Coprecipitation process fine magnetite particles: 4 g (particle size: 90 Å)

(B) F[CF(CF$_3$)CF$_2$O]nCF(CF$_3$)COONa (n: 8 on average): 1 g (C) F[CF(CF$_3$)CF$_2$O]pCF(CF$_3$)CH$_2$OSO$_3$Na: 5 g (p: 15 on average)

(D) Perfluoropolyether base oil: 30 g (BARRIERTA J100V)

The magnetic fluid thus obtained was subjected to measurement of vacuum degree and torque in the same manner as in Example 1. It was found that there was no change in the vacuum degree with the percent torque change being less than 3%

The Component (C) was prepared in the following manner:

A solution containing 26.5 g of hexafluoropropene oxide oligomer carboxylic acid (terminal group: —COOH; p: 15 on average) in 100 g of diglyme was cooled to 0° C., and a solution containing 0.9 g of LiAlH$_4$ in 30 g of diglyme was slowly dropwise added thereto with stirring for 3 hours. The reaction mixture was heated to 40° C. and stirring was continued for further 3 hours. Then, the reaction mixture was cooled again to 0° C. and 10 g of water was carefully dropwise added thereto. The reaction solvent was distilled off and the residues were dissolved into 100 g of a fluorine-based solvent (Fluorinert FC72), and insoluble matters were filtered off, whereby a solution containing hexafluoropropene oxide oligomer alcohol derivative (terminal group: —CH$_2$OH) as dissolved therein was obtained.

To the solution of the alcohol derivative were added 150 g of diglyme and 1.2 g of concentrated sulfuric acid, and the mixture was heated to 100° C. to distill off the fluorine-based solvent (Fluorinert FC72). Reaction was carried out for 2 hours, while maintaining the remaining reaction mixture at 100° C., and then the reaction mixture was ice cooled. Then, a solution containing 0.48 g of sodium hydroxide in 30 g of methanol was added thereto, and stirring was continued for 2 hours. Then, the solvent was distilled off and simultaneous extraction with 200 ml of an aqueous NaCl saturated solution and 200 ml of a fluorine-based solvent (Fluorinert FC72) was carried out. The extract (fluorine-based solvent layer) was thoroughly dried over anhydrous sodium sulfate, and then the solvent was distilled off, whereby 20.3 g of the above-mentioned Component (C) was obtained (yield throughout all the steps: 74%).

EXAMPLE 6

In Example 5, 2.5 g of the following compound was used as Component (C), and the similar results were obtained:

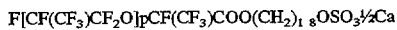

F[CF(CF$_3$)CF$_2$O]pCF(CF$_3$)COO(CH$_2$)$_{18}$OSO$_3$½Ca where p is 15 on average.

The Component (C) was prepared in the following manner:

A solution containing 3.14 g of 1,18-octadecanoic acid HOOC(CH$_2$)$_{16}$COOH in 100 g of diglyme was cooled to 0° C., and a solution containing 1.8 g of LiAlH$_4$ in 30 g of diglyme was slowly dropwise added thereto with stirring for 3 hours. Then, the reaction mixture was heated to 40° C. and stirring was continued for further 3 hours. Then, the reaction mixture was cooled again to 0° C., and 10 g of water was carefully dropwise added thereto. The reaction solvent was distilled off, and 100 g of chloroform and 50 g of water were added to the residues to dissolve them. Insoluble, decomposed matters (LiAlH$_4$) were filtered off, whereby a solution containing 1, 18-octadecaneglycol HO(CH$_2$)$_{18}$OH as dissolved therein was obtained.

To the glycol solution were added the same amount of the hexafluoropropene oxide oligomer carboxylic acid used in Example 5, 100 g of diglyme and 10 g of concentrated sulfuric acid, and the mixture was heated to 70° C. with vigorous stirring to distill off chloroform. Then, the reaction mixture was subjected to reaction at 120° C. for 5 hours, followed by cooling to room temperature and neutralization with an aqueous sodium hydrogen carbonate saturated solution. After most of the solvent was distilled off, simultaneous extraction with 200 ml of cold water and 200 ml of a fluorine-based solvent (Fluorinert FC72) was carried out. The extraction solvent (fluorine-based solvent) was distilled off, whereby 23.4 g of an intermediate product [terminal group: —COO(CH$_2$)$_{18}$OH] was obtained (yield throughout all the steps: 80%).

To the thus obtained intermediate product were added 100 g of a fluorine-based solvent (Fluorinert FC72), 150 g of diglyme and 0.94 g of concentrated sulfuric acid. Then, the mixture was heated at 100° C. to distill off the fluorine-based solvent (Fluorinert FC72). The reaction mixture was subjected to reaction for 2 hours, while maintaining the reaction mixture at 100° C., and then ice cooled. 0.25 g of calcium hydride was added thereto, and stirring was carried out for 2 hours. Insoluble matters were removed therefrom by decantation and then the solvent was distilled off, followed by simultaneous extraction with 200 ml of an aqueous NaCl saturated solution and with 200 ml of a fluorine-based solvent (Fluorinert FC72). The extract (fluorine-based solvent layer) was thoroughly dried over anhydrous sodium sulfate, and then the solvent was distilled off, whereby 21.2 g of the above-mentioned Component (C) was obtained (yield throughout all the steps: 70%).

EXAMPLE 7

In Example 5, the same amount of the following compound was used as Component (C) and similar results were obtained:

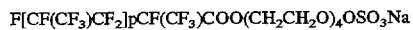

F[CF(CF$_3$)CF$_2$]pCF(CF$_3$)COO(CH$_2$CH$_2$O)$_4$OSO$_3$Na where p is 15 on average.

The Component (C) was prepared in the following manner:

To a solution containing 1.9 g of tetraethyleneglycol HO(CH$_2$CH$_2$O)$_4$H and 0.1 g of sodium methoxide in 100 g of diglyme was dropwise added 26.5 g of hexafluoropropene oxide oligomer carboxylic acid (terminal group: —COOH; p: 15 on average), and the mixture was heated to 80° C. and stirred for 5 hours, while removing generated methanol therefrom. After the solvent was distilled off, simultaneous extraction with 200 ml of cold water admixed with 10 ml of 1N hydrochloric acid and with 200 m of a fluorine-based solvent (Fluorinert FC72) was carried out. The extract (fluorine-based solvent layer) was washed with water twice. The solvent was distilled off therefrom, whereby 26.1 g of an intermediate product [terminal group: —COO(CH$_2$CH$_2$O)$_4$H] was obtained (yield: 92%).

The thus obtained intermediate product was dissolved into 150 g of diglyme, and then 1.08 g of concentrated sulfuric acid was added thereto. The mixture was heated to 100° C. with stirring and subjected to reaction for 2 hours, while maintaining that temperature. Then, the reaction mixture was ice cooled and a solution containing 0.44 g of sodium hydroxide in 30 g of methanol was added thereto, and stirring was continued for 2 hours. The solvent was distilled off therefrom and simultaneous extraction of the residues with 200 ml of an aqueous NaCl saturated solution and with 200 ml of a fluorine-based solvent (Fluorinert FC72) was carried out. The extract (fluorine-based solvent layer) was thoroughly dried over anhydrous sodium sulfate, and then the solvent was distilled off, whereby 22.5 g of the above-mentioned Component (C) was obtained (yield throughout all the steps: 76%).

EXAMPLE 8

In Example 5, the same amount of the same compound (n: 15 on average) was used as Component (B), and similar results were obtained.

Comparative Example 3

In Example 8, the Component (C) was not used at all. A magnetic fluid was obtained, but the vacuum degree after continuous operation was lowered to 10 Torr with the percent torque change being more than 10%.

EXAMPLE 9

A mixture consisting of the following Components (A) to (D) was subjected to a dispersion treatment under application of ultrasonic waves for 24 hours, whereby 89.7 g of fluorine-based magnetic fluid was obtained:

(A) Coprecipitation process fine magnetite perticles: 4 g (particle size: 90 Å)

(B) $F[CF(CF_3)CF_2O]nCF(CF_3)COONa$ (n:8 on average): 1 g (C) $F[CF(CF_3)CF_2O]pCF(CF_3)CH_2OPO(OH)_2$: 5 g (p: 15 on average)

(D) Perfluoropolyether base oil: 30 g (BARRIERTA J100V)

The Component (C) was prepared in the following manner:

26. 5 g of carboxylic acid (terminal group: —COOH) obtained by hydrolysis of methyl ester of hexafluoropropene oxide oligomer carboxylic acid (p: 15 on average) was dissolved into 100 g of diglyme, and a solution containing 1.2 g of $LiAlH_4$ in 30 g of diglyme was slowly dropwise added thereto, while maintaining the solution at 0° C. Stirring was carried out for 3 hours and then the mixture was heated to 40% : followed by stirring for further 3 hours. Then, the reaction mixture was cooled again to 0° C., and 10 g of water was carefully dropwise added thereto. The solvent was distilled off therefrom under reduced pressure, and 100 g of a fluorine-based solvent (Fluorinert FC72) was added thereto to dissolve the product. Insoluble matters were filtered off and the solvent was distilled off, whereby a perfluoroether alcohol derivative (terminal group: —$CH_2OH$) was obtained.

8 g of phosphorus pentoxide and 10 g of phosphoric acid were mixed together at 80° C. with stirring and the thus obtained perfluoroether alcohol derivative was slowly added thereto. Reaction was carried out for 5 hours. The reaction mixture was cooled to 0° C., and then 20 ml of cold water was added thereto. The mixture was stirred for 30 minutes, while heating the mixture up to room temperature. Then, the reaction mixture was extracted with a fluorine-based solvent (Fluorinert FC72), and the extract was thoroughly dried over anhydrous sodium sulfate, followed by distilling off of the solvent, whereby 23.3 g of a product was obtained as the above-mentioned Component (C) (yield throughout all the steps: 86%).

The fluorine-based magnetic fluid thus obtained was filled into a space formed between a shaft having a diameter of 15 mm and a seal assembly of pole piece-permanent magnet-pole piece as inserted along the shaft to make a vacuum seal, and then the vacuum seal was placed in a vacuum seal-evaluating apparatus and put into an intermittent operation for 500 hours, based on a cycle of continuous operations under such conditions of 0.01 Torr and 500 rpm, each for 25 minutes and in-between rests, each for 5 minutes, to determine the vacuum degree and torque. It was found that there was no change in the vacuum degree with the percent torque change being less than 3%.

EXAMPLE 10

In Example 9, the same amount of the following compound was used as Component (C) and similar results were obtained:

$F[CF(CF_3)CF_2O]pCF(CF_3)COO(CH_2)_6OPO(ONa)_2$ where p is 15 on average.

The Component (C) was prepared in the following manner:

26.5 g of carboxylic acid (terminal group: —COOH) obtained by hydrolysis of methyl ester of hexafluoropropene oxide oligomer carboxylic acid (p: 15 on average), 4.7 g of 1,6-hexanediol and 10 g of concentrated sulfuric acid were added to 200 g of diglyme, and the mixture was subjected to reaction at 120° C. for 5 hours with vigorous stirring. Then, the reaction mixture was cooled to room temperature and neutralized with an aqueous sodium hydrogen carbonate saturated solution. After most of the solvent was distilled off from the reaction mixture, simultaneous extraction with 200 ml of cold water and with 200 ml of a fluorine-based solvent (Fluorinert FC72) was carried out. Then, the extraction solvent (fluorine-based solvent) was distilled off under reduced pressure, whereby 25.0 g of 6-hydroxyhexyl ester of perfluoroether carboxylic acid [terminal group: —COO$(CH_2)_6OH$] was obtained (yield: 91%).

8 g of phosphorus pentoxide and 10 g of phosphoric acid were mixed with stirring, and the thus obtained 6-hydroxyhexyl ester of perfluoroether carboxylic acid was slowly added thereto. The mixture was subjected to reaction for 5 hours. The reaction mixture was cooled to 0° C., and 20 ml of cold water was added thereto. The mixture was stirred for 30 minutes, while heating it to room temperature. The reaction mixture was neutralized with 1N NaOH and extracted with a fluorine-based solvent (Fluorinert FC72). The extract was thoroughly dried over anhydrous sodium sulfate and the solvent was distilled off, whereby 24.5 g of a product was obtained as the above-mentioned Component (C) (yield throughout all the steps: 85%).

EXAMPLE 11

In Example 9, a fluorine-based magnetic fluid was prepared, using the same amount of the following compound as Component (C):

$\{F[CF(CF_3)CF_2O]pCF(CF_3)CONH(CH_2)_6O\}tPO(ONa)u$ where p is 15 on average, t is 1.5 on average and u is 1.5 on average.

The thus prepared magnetic fluid was subjected to the same determination of the vacuum degree and torque as in Example 9, and it was found that there was no change in the vacuum degree with the percent torque change being less than 3%

The Component (C) was prepared in the following manner:

26.7 g of methyl ester of hexafluoropropene oxide oligomer carboxylic acid (p: 15 on average) was added to 100 g of diglyme and then 1.4 g of 6-hydroxyhexylamine was added thereto. The mixture was stirred at 70° C. for 5 hours, and then the solvent was distilled off, followed by simultaneous extraction with 200 ml of cold water admixed with 10 ml of 1N HCl and with 200 ml of a fluorine-based solvent (Fluorinert FC72). The extract (fluorine-based solvent layer) was washed with water twice and then the extraction solvent was distilled off, whereby 27.3 g of perfluoroether carboxylic acid 6-hydroxyhexylamide [terminal group: —CONH(CH$_2$)$_6$OH] was obtained (yield: 99%).

The thus obtained perfluoroether carboxylic acid 6-hydroxyhexylamide was dissolved into 100 g of diglyme, and then 8 g of phosphorus pentoxide was added thereto. The mixture was subjected to reaction at 80° C. for 5 hours. The reaction mixture was cooled to 0° C. and 20 ml of cold water was added. The mixture was stirred for 30 minutes, while heating the mixture to room temperature, and then neutralized with 1N NaOH. After most of the solvent was distilled off, simultaneous extraction with 200 ml of an aqueous NaCl saturated solution and with 200 ml of a fluorine-based solvent (Fluorinert FC72) was carried out. The extract (fluorine-based solvent layer) was thoroughly dried over anhydrous sodium sulfate and the solvent was distilled off, whereby 27.5 g of a product was obtained as the above-mentioned Component (C) (yield throughout all the steps: 97%).

EXAMPLE 12

In Example 9, the same amount of the same compound (n: 15 on average) was used as Component (B), and similar results were obtained.

Comparative Example 4

In Example 12, the Component (C) was not used at all. A magnetic fluid was obtained, but the vacuum degree was lowered to 10 Torrr with the percent torque change being more than 10%.

What is claimed is:

1. A fluorine-based magnetic fluid, which comprises (A) fine magnetic particles dispersed in (D) a perfluoropolyether base oil represented by the following general formula:

F(CF(CF$_3$)CF$_2$O)$_m$Rf where Rf is a perfluoroalkyl group; m is an integer of 1 or more, by means of (B) a perfluoroether carboxylic acid or salt thereof represented by the following general formula:

F(CF(CF$_3$)CF$_2$O)$_n$CF(CF$_3$)COOM where M is a hydrogen atom, an alkali metal or an ammonium group; and n is an integer of 1 to 100, and (C) a perfluoroether (poly)alkylene ether carboxylic acid or salt thereof represented by the following general formula:

F(CF(CF$_3$)CF$_2$O)$_p$CF(CF$_3$)X(RO)$_q$CH$_2$COOM' where R is a lower alkylene group; M' is a hydrogen atom, an alkali metal, an alkaline earth metal or an ammonium group; X is COO group or CH$_2$O group; p and q are an integer of 1 to 100, respectively.

2. A fluorine-based magnetic fluid according to claim 1, wherein the magnetic particles are fine ferrite particles.

3. A fluorine-based magnetic fluid according to claim 1, wherein about 10 to about 100 parts by weight of the salt of perfluoroether carboxylic acid is used per 100 parts by weight of the fine magnetic particles.

4. A fluorine-based magnetic fluid according to claim 1, wherein about 1 to about 150 parts by weight of the perfluoroether (poly)alkylene ether carboxylic acid or salt thereof are used per 100 parts by weight of the perfluoropolyether base oil.

5. A fluorine-based magnetic fluid, which comprises (A) fine magnetic particles dispersed in (D) a perfluoropolyether base oil represented by the following general formula:

F(CF(CF$_3$)CF$_2$O)$_m$Rf where Rf is a perfluoroalkyl group; m is an integer of 1 or more, by means of (B) a perfluoroether carboxylic acid or salt thereof represented by the following general formula:

F(CF(CF$_3$)CF$_2$O)$_n$CF(CF$_3$)COOM where M is a hydrogen atom, an alkali metal or an ammonium group; and n is an integer of 1 to 100, and (C) an ester of perfluoroether sulfuric acid or salt thereof represented by the following general formula:

F(CF(CF$_3$)CF$_2$O)$_p$CF(CF$_3$)(Y)$_r$R'OSO$_3$M' where R' is a two-valent organic group; M' is a hydrogen atom, an alkali metal, an alkaline earth metal or an ammonium group; Y is COO group or CONH group; p is an integer of 1 to 100; r is 0 or 1.

6. A fluorine-based magnetic fluid according to claim 5, wherein the fine magnetic particles are fine ferrite particles.

7. A fluorine-based magnetic fluid according to claim 5, wherein about 10 to about 100 parts by weight of the salt of perfluoroether carboxylic acid is used per 100 parts by weight of the fine magnetic particles.

8. A fluorine-based magnetic fluid according to claim 5, wherein about 0.1 to about 50 parts by weight of the ester of perfluoroether sulfuric acid or salt thereof are used per 100 parts by weight of the perfluoropolyether base oil.

9. A fluorine-based magnetic fluid, which comprises (A) fine magnetic particles dispersed in (D) a perfluoropolyether base oil represented by the following general formula:

F(CF(CF$_3$)CF$_2$O)$_m$Rf where Rf is a perfluoroalkyl group; m is an integer of 1 or more, by means of (B) a perfluoroether carboxylic acid or salt thereof represented by the following general formula:

F(CF(CF$_3$)CF$_2$O)$_n$CF(CF$_3$)COOM where M is a hydrogen atom, an alkali metal or an ammonium group; and n is an integer of 1 to 100, and (C) an ester of perfluoroether phosphoric acid or salt thereof represented by the following general formula:

(F(CF(CF$_3$)CF$_2$O)$_p$CF(CF$_3$)(Y)$_t$(R)$_u$O)$_v$PO(OM')$_w$ where R is a lower alkylene group; M' is an hydrogen atom, an alkali metal, an alkaline earth metal or an ammonium group; Y is COO group or CONH group; p is an integer of 1 to 100; t is 1 or 2; u is 3- t; v and w are 0 or 1, respectively.

10. A fluorine-based magnetic fluid according to claim 9, wherein the fine magnetic particles are fine ferrite particles.

11. A fluorine-based magnetic fluid according to claim 9, wherein about 10 to about 100 parts by weight of the salt of perfluoroether carboxylic acid is used per 100 parts by weight of the fine magnetic particles.

12. A fluorine-based magnetic fluid according to claim 9, wherein about 1 to about 150 parts by weight of the perfluoroether compound is used per 100 parts by weight of the perfluoropolyether base oil.

* * * * *